United States Patent [19]

Sano

[11] 4,436,389
[45] Mar. 13, 1984

[54] OPHTHALMIC INSTRUMENT HAVING WORKING DISTANCE DETECTING MEANS

[75] Inventor: Eiichi Sano, Tokyo, Japan

[73] Assignee: Tokyo Kogaku Kikai Kabushiki Kaisha, Japan

[21] Appl. No.: 162,685

[22] Filed: Jun. 25, 1980

[30] Foreign Application Priority Data

Jun. 28, 1979 [JP] Japan .................................. 54-81631

[51] Int. Cl.³ .......................... A61B 3/14; G03B 29/00
[52] U.S. Cl. ....................................... 351/208; 354/62
[58] Field of Search .................. 351/7, 16, 13; 354/62

[56] References Cited

U.S. PATENT DOCUMENTS 4,219,258 8/1980 Araki et al. .............................. 351/7
4,257,687 3/1981 Kohayakawa ......................... 354/62

Primary Examiner—John K. Corbin
Assistant Examiner—Rodney B. Bovernick
Attorney, Agent, or Firm—Brumbaugh, Graves, Donohue & Raymond

[57] ABSTRACT

An ophthalmic instrument such as an eye fundus camera including an illuminating system which projects an illuminating light through a ring-shaped aperture to a patient's eye. There is provided a working distance detecting device which includes a light receiving section provided around the objective lens. A portion of the illuminating light as reflected at the cornea of the patient's eye is received by the light receiving section to determine a correct working distance.

8 Claims, 4 Drawing Figures

OPHTHALMIC INSTRUMENT HAVING WORKING DISTANCE DETECTING MEANS

The present invention relates to an ophthalmic instrument and more particularly to a working distance detecting device for such ophthalmic instruments.

In ophthalmic instruments such as eye fundus cameras, illumination light is projected through an objective lens to a patient's eye and, in case of an eye fundus camera, the light reflected at the eye fundus is directed again through the objective lens to the photographing optical system. In eye fundus cameras and other ophthalmic instruments in which the illumination light is projected through the objective lens and the light reflected at the eye fundus is directed to the photographing or observing optical system, a portion of the illumination light is reflected at the cornea of the patient's eye and such reflected light may be allowed to enter the photographing or observing optical system to thereby cause a flare or ghost in the image plane.

In conventional instruments, in order to eliminate the problem of such flare or ghost which is caused by the light reflected at the cornea of the patient's eye, the illumination system includes a ring-shaped aperture and an apertured mirror is obliquely disposed along the optical axis of the objective lens at a position conjugate with the pupil of the patient's eye with respect to the objective lens, so that the illumination light bundle is once focused at the annular reflecting surface of the mirror to be reflected thereby toward the objective lens. According to the arrangement, it is possible to eliminate the flare or ghost caused by the illumination light reflected at the cornea of the patient's eye when the apertured mirror is substantially conjugate with the pupil of the patient's eye with respect to the objective lens or, in other words, when the working distance between the objective lens and the pupil of the patient's eye is appropriately determined.

Thus, in this type of ophthalmic instruments, it is very important to maintain the correct working distance. Hithertofore, such correct distance has been established through a fine adjustment of the instrument while watching the image produced by the observing optical system. In case where the illumination is made by an infrared ray, the image to be watched is produced on a monitoring TV and, where the illumination is made by a visible light, the image is produced on an image plane to be watched through an eye lens. In the conventional arrangement, however, since it is required to perform complicated adjustments for the alignment between the patient's eye and the optical axis of the objective lens and for focusing together with the adjustment for the working distance, it is very likely that a faint flare or ghost is often looked over. Further, in ophthalmic instruments wherein the adjustments for the alignment and focusing are performed under the illumination by an infrared ray, it has been very difficult to detect the light scattered at the cornea or lens of the patient's eye in an image on a monitoring TV.

It is therefore an object of the present invention to provide convenient means for detecting a correct working distance in ophthalmic instruments.

Another object of the present invention is to provide an ophthalmic instrument in which a correct working distance can be determined by a reflection of the illumination light at the cornea of the patient's eye.

According to the present invention, the above and other objects can be accomplished by an ophthalmic instrument comprising objective lens means adapted to be located adjacent a patient's eye having a cornea with a working distance between the objective lens means and the patient's eye, an illuminating system including light source means and ring-shaped aperture means located substantially in conjugate with the patient's eye with respect to said objective lens means so that illumination light is projected through said aperture means and said objective lens means to the patient's eye, working distance detecting means including light receiving means provided around the objective lens means for detecting location of the light as reflected at the cornea of the patient's eye to determine the working distance. The light receiving means may be comprised of an annular plate located around the objective lens means coaxially therewith. In this instance, a correct working distance can be established when the illumination light reflected at the cornea of the patient's eye is at a predetermined radial position with respect to the optical axis of the objective lens. Conveniently, the light receiving plate may be provided with a circular mark coaxially with the optical axis of the objective lens. The light receiving plate may be directly observed or the light on the plate may be directed to the image plane of the observing optical system.

In another mode of the present invention, the light receiving means may be comprised of one end of a bundle of optical fibers, the other end of the bundle being located against the image plane of the observing optical system. Further, the light receiving means may be in the form of photoelectric elements which are associated with light emitting elements, of which lights are directed into the observing optical system. It is preferable that the photoelectric elements be arranged in a plurality of pairs, the elements in each pair being located adjacent to each other on the same radial line and the pairs being circumferentially spaced around the objective lens means, whereby the light as reflected at the cornea of the patient's eye reaches only one of the elements in each pair when the correct working distance is established. According to the present invention, it is possible to determine not only the working distance but also the alignment between the patient's eye and the axis of the objective lens means.

The above and other objects and features of the present invention will become apparent from the following descriptions of preferred embodiments taking reference to the accompanying drawings, in which.

Figure 1:
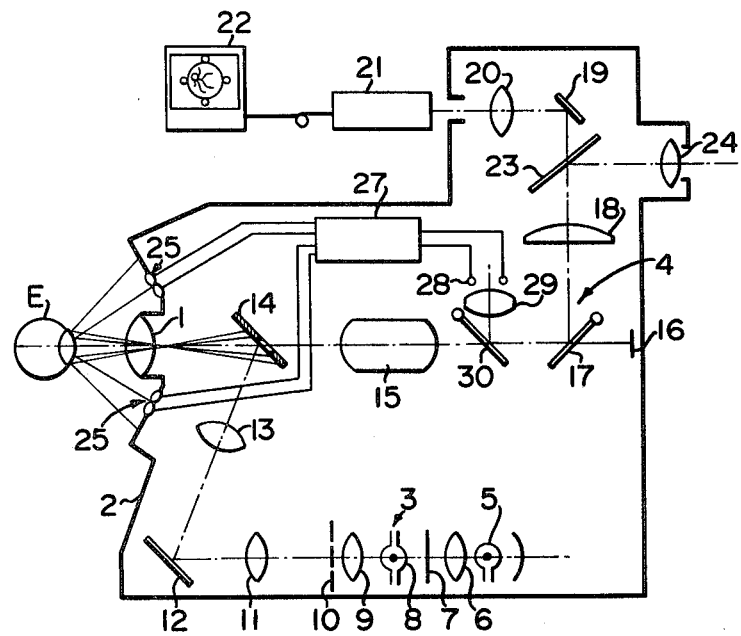
FIG. 1 is a diagrammatical sectional view showing the optical system of an eye fundus camera embodying the features of the present invention.

Referring now to the drawings, particularly to FIG. 1, there is disclosed an example wherein the present invention is applied to an eye fundus camera which includes an objective lens 1 mounted on a housing 2 and adapted to be placed adjacent a patient's eye E. In the housing 2, there are provided an illuminating optical system 3 and an observing and photographing optical system 4. The illuminating optical system 3 includes an observation illuminating light source 5 and a photographing light source 8. A condenser lens 6 and a red filter 7 are disposed between the light sources 5 and 8. The light from each of the light sources passes through a condenser lens 9 and a ring-shaped aperture 10 to a relay lens 11, and then through a reflecting mirror 12 and a relay lens 13 to an apertured mirror 14 which is obliquely located on the optical axis of the objective lens 1. The apertured mirror 14 has an annular reflecting surface on which the illuminating light produces a ring-shaped image. The light is then reflected at the annular reflecting surface of the mirror 14 toward the objective lens 1 so as to be projected therethrough to the patient's eye E.

The light is reflected at the fundus of the eye E and enters through the objective lens 1 and the aperture in the mirror 14 into the optical system 4. The system 4 includes a focusing lens 15 through which the light is passed to a photographing film plane 16 to produce an image of the eye fundus. In front of the film plane 16, there is obliquely disposed a retractable mirror 17 which is adapted to reflect the light from the lens 15 upwardly to a field lens 18 so that an image is produced on the image plane of the field lens 18. The light which has passed through the field lens 18 is reflected by a mirror 19 and passed through an imaging lens 20 to a taking tube 21. The taking tube 21 produces a signal which is transmitted to a monitoring TV to produce a visible image thereon. Between the field lens 18 and the mirror 19, there is obliquely disposed a further mirror 23 which reflects the light toward an eyepiece 24 for observation. The mirror 23 is retractable from the optical path whenever desired.

Figure 2:
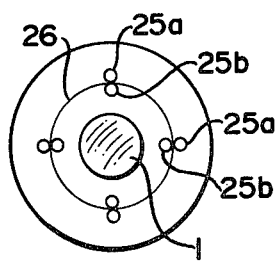
FIG. 2 is a front view of the light receiving section showing an example of the arrangement of the photoelectric elements.

Around the objective lens 1, there is provided a light receiving section which includes a plurality of photoelectric elements 25. As shown in FIG. 2, the photoelectric elements 25 are arranged in pairs comprising elements 25a and 25b which are located adjacent to each other on the same radial line. Four pairs of elements are located along a circle coaxial with the optical axis of the objective lens 1 with angular spaces of 90°. A portion of the illuminating light is reflected at the corneal surface of the patient's eye E toward the objective lens 1 to produce an image having a circular inner periphery as shown at 26 in FIG. 2. The diameter of the inner periphery of the image increases in accordance with an increase in the distance between the objective lens 1 and the patient's eye. The positions of the elements 25a and 25b in each pair are determined in such a manner that the inner periphery 26 is between the elements 25a and 25b when objective lens 1 is at the correct working distance with respect to the patient's eye E.

Each pair of the photoelectric elements 25 is connected with a light emitting element 28 through a detecting circuit 27 which gives a signal to the element 28 when the light is applied to only one of the paired elements 25a and 25b. It should therefore be understood that all of the elements 28 are energized only when the correct working distance is established. The light from the elements 28 is transmitted through a relay lens 29 to a half-transparent mirror 30 which is behind the focusing lens 15 to be reflected toward the mirror 17. Thus, the operator is able to know whether the working distance is correct or not simultaneously observing the image of the eye fundus.

Figure 3:
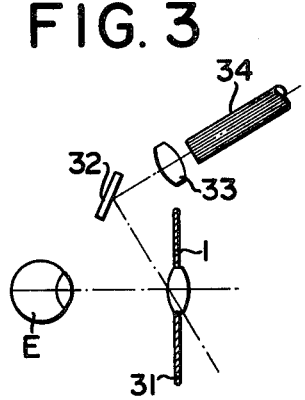
FIG. 3 is a fragmentary side view showing another embodiment of the present invention; and, FIG. 4 is a view showing a further embodiment of the present invention.

Referring to FIG. 3, there is shown another embodiment of the present invention. In this embodiment, there is provided a light receiving plate 31 which is disposed around the objective lens 1. The plate 31 may conveniently be provided with a mark such as a circle at a position where the inner periphery of the reflection at the cornea of the patient's eye E comes under the correct working distance. The plate 31 may be directly observed or, as shown in FIG. 3, the reflection at the plate 31 may be transmitted through a mirror 32 and a relay lens 33 to a bundle of glass fibers 34 to thereby direct the image of the light reflected at the cornea to a desired place. For example, the glass fiber bundle may be led to the field lens in the observing optical system so that the image on the plate 31 may be observed simultaneously with the image of the eye fundus.

Figure 4:
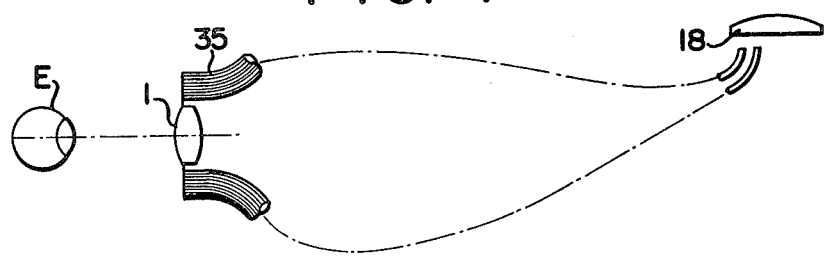

FIG. 4 shows a further embodiment of the present invention in which the bundle 35 of the glass fibers has one end arranged in a circular form or at suitable circumferentially spaced positions, the other end of the bundle 35 being opposed to the image plane of the field lens 18. In this embodiment, it is also possible to observe the position of the reflection at the cornea of the patient's eye. Conveniently, a circular mark may be provided on the one end of the glass fiber bundle 35.

When an infrared ray is projected from the illumination system, there may be disposed a filter transparent to the infrared ray in the light receiving section or in the path for transmitting the light reflected at the cornea. By this arrangement, it becomes possible to detect only the infrared ray among the light reflected at the cornea of the patient's eye E.

The invention has thus been shown and described with reference to specific embodiments, however, it should be noted that the invention is in no way limited to the details of the illustrated arrangements but changes and modifications may be made without departing from the scope of the appended claims.

I claim:

1. An ophthalmic instrument comprising objective lens means adapted to be located adjacent a patient's eye having a cornea with a working distance between the objective lens means and the patient's eye, an illuminating system including light source means and ring-shaped aperture means located substantially in conjugate with the patient's eye with respect to said objective lens means so that illumination light is projected through said aperture means and said objective lens means to the patient's eye, working distance detecting means including light receiving means provided at a plurality of points around the objective lens means for detecting the location of a radially inner boundary of an image of said ring-shaped aperture means as produced around the objective lens means by the light projected from said illumination system and reflected at the cornea of the patient's eye, said light receiving means having means for detecting radial positions of at least a plurality of points of said radially inner boundary of the image to determine the working distance and the alignment between the optical axis of the eye an the optical axis of the instrument.

2. An ophthalmic instrument in accordance with claim 1 in which the light receiving means is comprised of an annular plate located around the objective lens means.

3. An ophthalmic instrument in accordance with claim 2 in which a relay optical system is provided for transmitting a reflection at the plate to observing means.

4. An ophthalmic instrument in accordance with claim 1 in which said light receiving means is comprised of one end of a bundle of optical fibers, the other end of the bundle being led to observing means.

5. An ophthalmic instrument in accordance with claim 1 in which said light receiving means is comprised of a plurality of photoelectric elements.

6. An ophthalmic instrument in accordance with claim 5 which further includes light emitting elements associated with the photoelectric elements, light from the light emitting elements being directed to observing means.

7. An ophthalmic instrument comprising objective lens means adapted to be located adjacent a patient's eye having a cornea with a working distance between the objective lens means and the patient's eye, an illuminating system including light source means and ring-shaped aperture means located substantially in conjugate with the patient's eye with respect to said objective lens means so that illumination light is projected through said aperture means and said objective lens means to the patient's eye, working distance detecting means including light receiving means comprised of a plurality of photoelectric elements provided around the objective lens means for detecting location of the light as reflected at the cornea of the patient's eye to determine the working distance, the photoelectric elements being arranged in a plurality of pairs, the elements in each pair being located adjacent to each other on the same radial line and the pairs being circumferentially spaced around the objective lens means, whereby the light as reflected at the cornea of the patient's eye reaches only one of the elements in each pair when the correct working distance is established.

8. An ophthalmic instrument in accordance with claim 7 in which each pair of the photoelectric elements is associated with a light emitting element through control means which applies an energizing signal to the light emitting element when only one of the photoelectric elements in the pair is illuminated.

* * * * *